United States Patent [19]

Kool et al.

[11] Patent Number: 5,100,915

[45] Date of Patent: Mar. 31, 1992

[54] REDUCTION AND INHIBITION OF ETU CONTENT IN ALKYLENEBISDITHIOCARBAMATES

[75] Inventors: Pieter Kool; Pieter C. Diepenhorst, both of Zuid Holland; Jacobus A. M. Nouws, Etten-leur, all of Netherlands

[73] Assignee: Pennwalt France S.A., Plaisir, France

[21] Appl. No.: 533,967

[22] Filed: Jun. 6, 1990

[51] Int. Cl.$^5$ .............................................. A01N 47/10
[52] U.S. Cl. ...................................... 514/476; 514/973
[58] Field of Search ........................ 514/392, 476, 973

[56] References Cited

U.S. PATENT DOCUMENTS

| | | | |
|---|---|---|---|
| 2,579,384 | 12/1951 | Handy et al. | 260/29.7 |
| 3,085,042 | 4/1963 | Luginbuhl | 167/22 |
| 3,210,394 | 10/1965 | Nemec et al. | 260/429 |
| 3,379,610 | 4/1966 | Lyon et al. | 167/22 |
| 3,523,960 | 8/1970 | Lehureau | 260/429 |
| 3,856,851 | 12/1974 | Buchman et al. | 260/513.5 |
| 3,869,486 | 3/1975 | Van den Boogaart et al. | 260/429 |
| 4,185,113 | 1/1980 | Virrion et al. | 424/286 |
| 4,217,293 | 8/1980 | Adams, Jr. | 260/429 |
| 4,344,890 | 8/1982 | Adams, Jr. | 260/429 |
| 4,655,935 | 4/1987 | Wijn et al. | 210/750 |

FOREIGN PATENT DOCUMENTS 890669 2/1982 Belgium .
0008533 3/1980 European Pat. Off. .

OTHER PUBLICATIONS

Kumin, T. I., "Studies on the Production of Rongalite [HMS]", *Zhur. Priklad. Khim.*, 21:685-91 (1948).
Marshall, W. D., "Thermal Decomposition of Ethylenebisdithiocarbamate Fungicides to Ethylenethiourea in Aqueous Media", *J. Agric. Food Chem.*, 25(2):357-61 (1977).
Hylin, J. W., "Oxidative Decomposition of Ethylene-Bis-Dithiocarbamates", *Bull. Envir. Contam. & Toxic*, 10(4):227-33 (1973).
Merck Index, 10th Edition, #8454.

*Primary Examiner*—Frederick E. Waddell
*Assistant Examiner*—T. J. Criares
*Attorney, Agent, or Firm*—Panitch Schwarze Jacobs & Nadel

[57] ABSTRACT

A method is provided for stabilizing alkylenebisdithiocarbamates, such as 1,2-ethylenebisdithiocarbamates (EBDC), by mixing the EBDC in the presence of water with a hydroxymethane sulfinate (HMS) which degrades to formaldehyde to reduce the content of ethylenethiourea (ETU) in the EBDC. The HMS and sulfate by-product from the formaldehyde formation also act as reducing agents to inhibit further ETU formation by oxidative decomposition of EBDC. The hydroxymethane sulfinate is preferably added in an amount of about 0.1 to 5 weight percent based upon the EBDC, and the aqueous reaction mixture is then preferably dried under vacuum. Co-polymerization agents, such as hydroquinone or melamine, may also be added to further reduce and inhibit ETU content and formation.

25 Claims, No Drawings

REDUCTION AND INHIBITION OF ETU CONTENT IN ALKYLENEBISDITHIOCARBAMATES

CROSS-REFERENCE TO RELATED APPLICATION

This application is related to our co-pending application Ser. No. 492,526, filed Mar. 12, 1990, now U.S. Pat. No. 5,021,599, for "Enhanced Reduction and Inhibition of ETU Content in Alkylenebisdithiocarbamates."

FIELD OF THE INVENTION

The present invention relates to the reduction and inhibition of the content of alkylenethioureas (2-imidazolidinethiones) in alkylenebisdithiocarbamates. More particularly, the present invention relates to the reduction of the content of ethylenethiourea (ETU) in 1,2-ethylenebisdithiocarbamates. The present invention is also directed to a method of obtaining and stabilizing the ETU content at very low levels, preferably less than 0.015 weights percent, in alkylenebisdithiocarbamate formulations.

BACKGROUND OF THE INVENTION

Various salts of 1,2-ethylenebisdithiocarbamic acid have been known for many years as agents for combating plant diseases caused by fungi. Among the ethylenebisdithiocarbamates (sometimes referred to as "EBDC") useful as plant fungicides are the manganese, zinc, nickel, cobalt, copper, sodium, potassium and ammonium salts of 1,2-ethylenebisdithiocarbamic acid or co-reacted metal EBDC. Preferred fungicides of this class are manganese EBDC (maneb), zinc EBDC (zineb), and particularly zinc coordination complexes of manganese EBDC (mancozeb). Disodium EBDC (nabam), an intermediate in the production of maneb, zineb and mancozeb, also has fungicidal properties.

A problem with the EBDCs is that they tend to degrade over time due to factors including oxidation, heat, humidity, etc., into, among other things, ethylenethiourea (2-imidazolidinethione), commonly known as ETU. Due to this degradation, ETU content increases in concentration during storage of the EBDC. Since ETU has been found to have carcinogenic and teratogenic effects in laboratory animals, and no significant biological activity as a fungicide has been observed, ETU is an unwanted degradation product.

Over the years a number of processes and additives have been developed to reduce the ET content of EBDCs. It is desirable that the ETU content of EBDC formulations be reduced to less than 0.015 percent by weight, based on the weight of the EBDC in the formulation. Several prior attempts have been made to reduce the content of ETU in EBDC by adding formaldehyde or a formaldehyde donor to the aqueous reaction mixture, preferably with a water-soluble zinc salt, and also by optionally adding paraformaldehyde or another formaldehyde donor, for example, a formaldehyde precursor or a formaldehyde generator, to the dried product. See, for example, U.S. Pat. Nos. 4,217,293 and 4,344,890 of Adams. Moreover, hexamethylenetetramine (a formaldehyde donor in the presence of water) is commonly used in EBDC formulations (e.g., PENNCOZEB) as a thermal stabilizer and can react with ETU.

More effective processes of reducing ETU content in EBDC are desired which do not have the disadvantages of formaldehyde, such as pungent smell and toxic vapors.

SUMMARY OF THE INVENTION

According to the present invention, a method is provided for stabilizing alkylene-bisdithiocarbamates by mixing with the EBDC in the presence of water an amount of hydroxymethane sulfinate (HMS), preferably the sodium salt dihydrate (SHMS), which will degrade to sufficient formaldehyde to reduce the content and retard the formation of ETU in the EBDC. The HMS is preferably added in an amount of about 0.1 to 5 weight percent based on the weight of EBDC and may be added alone to undried EBDC or an aqueous formulation of EBDC, or may be added with water to dried EBDC.

A co-polymerization agent such as hydroquinone or melamine may also be mixed with the EBDC. To obtain a stabilized dry product, the mixture is preferably vacuum dried. The products ultimately contain residual HMS, mono- and/or bis-N-methylolalkylenethioureas and polymerization products thereof, sulfite, and less than about 0.015 weight percent alkylenethiourea per se.

DETAILED DESCRIPTION OF PREFERRED EMBODIMENTS

Fungicidal salts of 1,2-ethylenebisdithiocarbamic acid are well known in the art and commercially available from a number of agricultural chemical companies, including Atochem North America, Inc. (formerly Pennwalt Corporation), Rohm & Haas Company, E.I. duPont de Nemours & Company, Roussel UCLAF, etc. Particularly preferred are the zinc and manganese coordination complexes of EBDC (mancozeb) which may be made by various processes, such as those described in U.S. Pat. Nos. 3,210,394; 3,379,610 and 3,869,486.

These fungicides are available in various forms, including aqueous liquid formulations (suspension concentrates ("SC")) and dry wettable powders ("WP"). An example of one commercially available fungicide of this type is "PENNCOZEB" fungicide, a product available from Atochem North America, Inc. PENNCOZEB contains 80 percent active ingredient of a coordination product of maneb and a zinc salt consisting of 16 percent manganese ions, 2 percent zinc ions, 62 percent ethylenebisdithiocarbamate ($C_4H_6N_2S_4$) ions and 20 percent inert ingredients.

However, it will be understood that the present invention is applicable to any alkylenebisdithiocarbamate, particularly 1,2-alkylenebisdithiocarbamates, which contains or yields ethylenethiourea (ETU) or ETU-like products as a degradation product. Other such alkylenebisdithiocarbamates, which can be considered as homologues of ethylenebisdithiocarbamates, include propineb (zinc 1-methyl-1,2-ethylenebisdithiocarbamate) which produces methyl-ETU, and metiram (zineb-ethylene thiuram disulfide adduct). For ease of reference herein, all of the alkylenebisdithiocarbamates and homologues which contain or yield ETUs will be referred to as "EBDCs." Similarly, all alkylenethioureas or like products will be referred to herein as "ETUs."

The present invention is based partly upon the inhibition of the formation of ETU by oxidative decomposition reaction due to the reductive capacity of HMS. In addition, the present invention is based upon the known reaction of ETU with formaldehyde directly or from formaldehyde donors. For example, PENNCOZEB formulations always contain a thermal stabilizer, namely hexamethylenetetramine, which in the presence of water is a formaldehyde donor which will react with ETU.

According to the present invention, a product which slowly degrades or disintegrates to formaldehyde is added to the EBDC, preferably as a solution. In particular, an HMS is mixed with the EBDC. The HMS may be an alkali metal or an alkaline-earth metal salt of hydroxymethane sulfinic acid, for example, the sodium, calcium, magnesium or potassium salt of HMS. The HMS may also be a zinc salt. The cobalt, magnesium and zinc complexes of hydroxymethane sulfinic acid are also known, and may be used in accordance with the present invention. Preferably, the HMS used in the present invention is the sodium salt dihydrate (SHMS).

The HMS is oxidized by air or by the oxidation products of EBDC in the presence of water to a hydroxymethane sulfonate, which in turn degrades to formaldehyde and a sulphite salt. Thus, the HMS protects the EBDC from oxidative decomposition by oxygen in air. The formaldehyde then reacts with ETU to form various condensation products.

An aqueous medium for the HMS/EBDC 0 mixture can be provided in any of a number of ways, including, for example:

(1) HMS may be added to the undried EBDC product, which is generally an aqueous paste (about 25 percent water) obtained from the reaction mixture for forming the EBDC;

(2) HMS may be added with water to the dried EBDC;

(3) HMS may be added alone to liquid aqueous dispersions or other aqueous formulations containing the EBDC. Other possibilities will be evident to those skilled in the art based upon the present disclosure.

The HMS is mixed with the EBDC in an amount which will degrade to a sufficient amount of formaldehyde to react with any ETU which may be present in the EBDC or which is likely to be formed as the EBDC degrades during the normal storage life of the EBDC product. Amounts of HMS in the range of about 0.1 to 5 weight percent based upon the weight of EBDC have been found to be satisfactory according to the present invention, and about 1 to 3 weight percent is generally sufficient.

The amount of water which must be present in the mixture of HMS and EBDC is that amount which is sufficient to allow conversion of HMS to formaldehyde and to allow good dispersion of the HMS throughout the EBDC formulation so that it will be available for further conversion to formaldehyde and retardation of ETU during storage. It is preferred that the mixture contain at least two hundred percent water by weight based upon the weight of the dry EBDC. This is sufficient to form an aqueous paste or a generally thick slurry of the EBDC.

So long as sufficient water is present, the aqueous medium need only remain for sufficient time to obtain good dispersion of the HMS with the EBDC. Generally, the HMS and EBDC mixture is mixed for a time to obtain a homogeneous mixture. The mixing is generally conducted at room temperature.

Thereafter, the mixture is dried, preferably under vacuum, to a powder. In accordance with the present invention, drying of EBDCs is conducted in the absence of oxygen and preferably, in the absence of oxygen and water. Oxygen, alone or in combination with water, decomposes EBDCs. Accordingly, a drying method to be used in the present invention comprises an oxygen-free environment, for example, a heated, inert gas environment, such as argon or nitrogen.

When the mixture is dried into a powder, the powder will generally contain about 0.5 to about 2.0 weight percent water. This water will then react with the homogeneously dispersed HMS to form formaldehyde. It is also possible to leave the EBDC undried as an aqueous formulation, for example, as a suspension concentrate or a suspo-emulsion. Generally, the suspension concentrate or suspo-emulsion has a water content of about 50 to about 70 weight percent, and preferably, a water content of about 50 to about 55 weight percent. Whether the mixture is dried or used as an aqueous formulation, oxygen and high temperatures should be avoided during drying and storage due to their degradative effects on the EBDC.

The method of the present invention may be illustrated by the following reaction equations. Influenced by oxidation products of EBDC and by water, HMS is first oxidized to hydroxymethane sulfonate, as shown in equation I below:

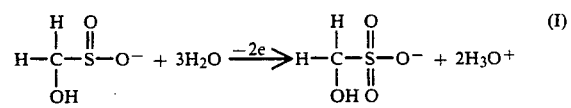
(I)

Hydroxymethane sulfonate then degrades to formaldehyde and the corresponding sulphite, also in the presence of water, as shown in equation II below:

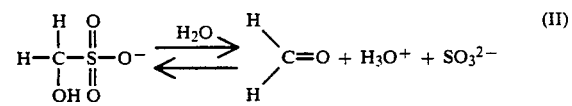
(II)

In accordance with the present invention, the reaction to prepare formaldehyde, described in equations I and II, will occur similarly if sodium or other hydroxymethane sulfonate is used as the starting material instead of HMS.

Reactions of formaldehyde with ETU are well known and are described, for example, in Kaplan et al. U.S. Pat. No. 3,004,002. These reactions include the formation of N-methylolethylenethiourea and N,N'-dimethylolethylenethiourea, as shown in equation III below:

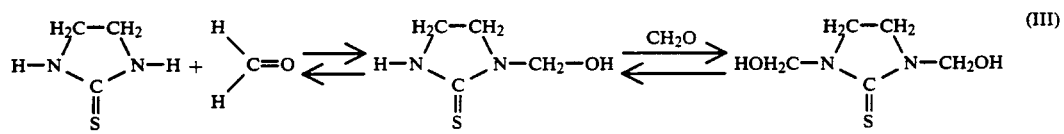
(III)

The reaction products of equation III have a strong tendency to polymerize and will, depending on the circumstances and concentrations, yield the reactions shown in equations IV and V below:

examples. These examples illustrate, inter alia, the effect on the ETU content of an EBDC with and without the

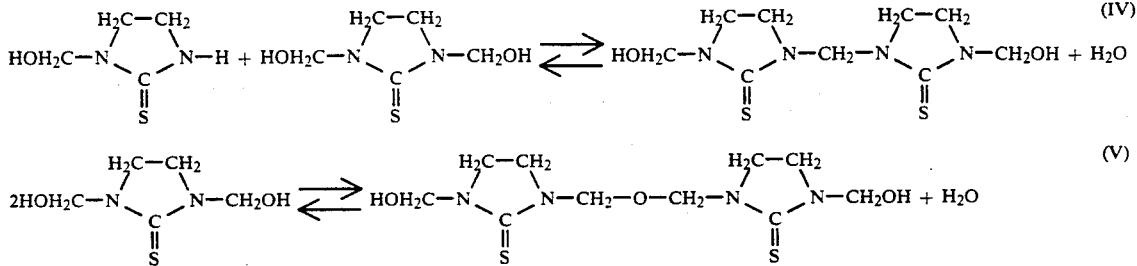

During storage, residual HMS inhibits the formation of ETU by preventing oxidative decomposition of the EBDC. The residual HMS may oxidize to hydroxymethane sulfonate, which is in equilibrium with formaldehyde (see equation II above). As indicated, formaldehyde inhibits the formation of ETU. As a result, the stabilized EBDC according to the present invention will contain unreacted or residual HMS, mono- and/or dimethylolalkylenethioureas, sulfite, and less than about 0.015 weight percent ETU per se based on the weight of the EBDC.

The advantage of using HMS for mixing with EBDC instead of using formaldehyde directly or paraformaldehyde is that the formaldehydes give an odor to the EBDC, whereas the HMS does not smell at all. Further, since HMS slowly disintegrates to formaldehyde, the formaldehyde is available for a longer period of time for reaction with ETU. Still further, HMS and sulphite have the advantage of being reducing agents which thereby inhibit the oxidation of EBDC so that the formation of ETU is retarded. Hence, oxidation of EBDC is hindered without the loss of formaldehyde.

According to another embodiment of the present invention, ETU can be further reduced to lower levels by the addition of one or more co-polymerization agents which force the polymerization reactions (equations IV and V above) of formaldehyde and ethylenethioureas to termination. Such co-polymerization agents are preferably nucleophilic active aromatic compounds including, for example, hydroquinone, melamine, benzoquinone, methoxyhydroquinone, 1,2-naphthoquinone, 1,4-naphthoquinone, pyrocatechol, resorcinol, phloroglucinol dihydrate, γ-pyran, N-mono- and N,N'-disubstituted melamines, such as N-butylmelamine and N,N'-dibutylmelamine, 2,4-diamino-1,3,5-triazines, such as 2,4-diamino-6-chloro-1,3,5-triazine, 2-phenoxy-4,6-diaminoI,1,3,5-triazine and ammeline, and ammelide. Hydroquinone and melamine are preferred co-polymerization agents.

The co-polymerization agent may be mixed with the aqueous reaction mixture in amounts of about 0.02 to 0.5 weight percent based on the weight of EBDC. When using such co-polymerization agents, the resulting EBDC formulation will also contain the co-polymerization agents.

The use of such co-polymerization agents may reduce the ETU content to less than about 0.007 weight percent ETU per se based on the weight of the EBDC. The use and reaction of such co-polymerization agents is more fully described in our co-pending application Ser. No. 492,526, the disclosure of which is incorporated herein by reference.

The present invention will now be illustrated with further reference to the following specific, non-limiting examples. These examples illustrate, inter alia, the effect on the ETU content of an EBDC with and without the addition of SHMS as a stabilizer.

EXAMPLE 1

To 4 grams of mancozeb (PENNCOZEB WP), initially containing 0.05 weight percent of ETU, were added 50 milligrams of SHMS and 10 ml of water. After 5 minutes mixing at room temperature, the wet paste was dried in a vacuum (10 mm Hg for 16 hours at 70° C.) resulting in a water content of 0.6 weight percent. Within 45 days, an ETU content of 0.010 weight percent was reached and remained stable for at least 286 days (0.006 weight percent ETU).

In contrast, a PENNCOZEB WP product, without the addition of SHMS stabilizer, had an ETU content of 0.11 weight percent directly. The ETU content increased to 0.14 weight percent after 31 days and increased further to 0.19 weight percent after 92 days. When PENNCOZEB WP was mixed dry with SHMS (without additional water), an ETU content of 0.085 weight percent was reached after 60 days and remained stable for at least 174 days (0.075 weight percent).

These results suggest that in the case of dry mixing, SHMS is not distributed as evenly throughout the mixture as in the case of addition of SHMS by aqueous solution. Thus, the SHMS is less accessible for the heterogeneous reaction with the small amount of water and ETU present. The SHMS slowly decomposes to formaldehyde and, consequently, the formaldehyde slowly reacts with the ETU. This accounts for the initial increase in ETU content at dry mixing and the subsequent slow decrease of ETU.

In addition, with dry mixing the temperature of the mixture can increase. Thus, there is a risk of faster decomposition of the EBDC to ETU, than where an aqueous solution of SHMS is employed.

EXAMPLE 2

To 4 grams of mancozeb (PENNCOZEB WP), containing 12 milligrams of paraformaldehyde and initially containing 0.05 weight percent of ETU, were added 100 milligrams of SHMS and 10 ml water. The added paraformaldehyde in this Example provides an initial concentration of formaldehyde before the SHMS degrades to formaldehyde. After 5 minutes mixing at room temperature, the wet paste was dried in a vacuum (10 mm Hg for 16 hours at 70° C.) to a water content of 0.6 weight percent. Within 45 days, an ETU content of 0.007 weight percent was reached and decreased slowly to 0.002 weight percent after 209 days.

For the same PENNCOZEB WP product, containing paraformaldehyde but without the addition of SHMS, an ETU content of 0.012 weight percent was reached in 3 days and remained stable for only 20 days (0.013 weight percent). After 31 days, the ETU content increased to 0.017 weight percent.

EXAMPLE 3

To 4 grams of mancozeb (PENNCOZEB WP), initially containing 0.05 weight percent of ETU, were added 10 milligrams hydroquinone, 50 milligrams SHMS and 10 ml water. After 5 minutes mixing at room temperature, the wet paste was dried in a vacuum (6 mm Hg for 16 hours at 70° C.) to a water content of 0.6 weight percent. Within 28 days, an ETU content of 0.007 weight percent was reached and decreased slowly to 0.004 weight percent after 286 days.

In contrast, a mancozeb sample, without the addition of SHMS stabilizer, had an ETU content of 0.11 weight percent directly. The ETU content increased to 0.14 weight percent after 31 days and increased further to 0.19 weight percent after 92 days. In a PENNCOZEB WP product without SHMS but with hydroquinone and containing 2 weight percent hexamethylenetetramine, an ETU content of 0.034 weight percent was reached after 10 days and increased slightly thereafter.

The present invention may be embodied in other specific forms without departing from the spirit or essential attributes thereof and, accordingly, reference should be made to the appended claims, rather than to the foregoing specification as indicating the scope of the invention.

We claim:

1. A method of stabilizing an alkylenebisdithiocarbamate comprising mixing with the alkylenebisdithiocarbamate in the presence of water an amount of hydroxymethane sulfinate which will degrade to sufficient formaldehyde to reduce the content and retard the formation of alkylenethioureas in the alkylenebisdithiocarbamate.

2. A method according to claim 1 wherein the alkylenebisdithiocarbamate is a salt of 1,2-ethylenebisdithiocarbamate.

3. A method according to claim 1 wherein the cation of the alkyenebisdithiocarbamate is selected from the group consisting of manganese, zinc, nickel, cobalt, copper, sodium, potassium, ammonium and co-reacted complexes thereof.

4. A method according to claim 3 wherein the alkylenebisdithiocarbamate is a co-reacted complex with manganese and zinc.

5. A method according to claim 1 wherein the hydroxymethane sulfinate is mixed in an amount of about 0.1 to 5 weight percent based on the alkylenebisdithiocarbamate.

6. A method according to claim 1 wherein the hydroxymethane sulfinate is mixed with an undried alkylenebisdithiocarbamate.

7. A method according to claim 1 wherein water and hydroxymethane sulfinate are mixed with the alkylenebisdithiocarbamate.

8. A method according to claim 1 wherein water is present in an amount of at least 200 weight percent based on the alkylenebisdithiocarbamate.

9. A method according to claim 1 wherein hydroxymethane sulfinate is mixed with an aqueous formulation of the alkylenebisdithiocarbamate.

10. A method according to claim 1 wherein the mixture is subsequently dried to a powder.

11. A method according to claim 10 wherein the mixture is vacuum dried.

12. A method according to claim 1 wherein said hydroxymethane sulfinate is selected from the group consisting of alkali metal salts, alkaline-earth metal salts, zinc salt, cobalt complex, magnesium complex, and zinc complex of hydroxymethane sulfinic acid.

13. A method according to claim 12 wherein said hydroxymethane sulfinate salt is sodium hydroxymethane sulfinate dihydrate.

14. A method according to claim 1 comprising further mixing the alkylenebisdithiocarbamate with a co-polymerization agent which forces the polymerization reaction of formaldehyde and alkylenethiourea to termination.

15. A method according to claim 14 wherein said co-polymerization agent is a nucleophilic active aromatic compound.

16. A method according to claim 15 wherein said nucleophilic active aromatic compound is selected from the group consisting of hydroquinone, benzoquinone, methoxyhydroquinone, 1,2-naphthoquinone, 1,4-naphthoquinone, pyrocatechol, resorcinol, phloroglucinol dihydrate, γ-pyran, melamine, N-monosubstituted melamines, N,N'-disubstituted melamines, 2,4-diamino-1,3,5triazines, and ammelide.

17. A method according to claim 16 wherein said N-monosubstitued melamine is N-butylmelamine.

18. A method according to claim 16 wherein said N,N'-disubstituted melamine is N,N'-dibutylmelamine.

19. A method according to claim 16 wherein said 2,4-diamino-1,3,5-triazine is selected from the group consisting of 2,4-diamino-6-chloro-1,3,5-triazine, 2-phenoxy-4,6-diamio-1,3,5-triazine and ammeline.

20. A method according to claim 14 wherein said co-polymerization agent is mixed in an amount of about 0.02 to 0.5 weight percent based on the weight of the alkylenebisdithiocarbamate.

21. A stabilized alkylenebisdithiocarbamate containing hydroxymethane sulfinate, mono- and/or bis-N-methylolalkylenethioureas and polymerization products thereof, sulfite, and less than about 0.015 weight percent alkylenethiourea per se based on the weight of the alkylenebisdithiocarbamate.

22. A stabilized alkylenebisdithiocarbamate according to claim 21 wherein said sulfinate is sodium hydroxymethane sulfinate dihydrate.

23. A stabilized alkylenebisdithiocarbamate according to claim 21 which is 1,2-ethylenebisdithiocarbamate.

24. A stabilized alkylenebisdithiocarbamate according to claim 21 which contains a co-polymerization agent selected from the group consisting of hydroquinone and melamine.

25. The method according to claim 1, wherein the aklylenebisdithiocarbamate contains or yields ethylenethiourea or ethylenethiourea-like products as degradation products.

* * * * *